US009710941B2

(12) United States Patent
Suzuki et al.

(10) Patent No.: US 9,710,941 B2
(45) Date of Patent: Jul. 18, 2017

(54) BIOLOGICAL INFORMATION DISPLAYING APPARATUS AND BIOLOGICAL INFORMATION DISPLAYING METHOD

(71) Applicant: NIHON KOHDEN CORPORATION, Tokyo (JP)

(72) Inventors: Takehito Suzuki, Tokyo (JP); Takashi Yaginuma, Tokyo (JP); Masahiro Yade, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/508,443

(22) Filed: Oct. 7, 2014

(65) Prior Publication Data

US 2015/0103095 A1 Apr. 16, 2015

(30) Foreign Application Priority Data

Oct. 15, 2013 (JP) ................................ 2013-214509

(51) Int. Cl.
 *G06T 11/00* (2006.01)
 *G06T 11/60* (2006.01)
 (Continued)

(52) U.S. Cl.
 CPC ........ *G06T 11/206* (2013.01); *A61B 5/02007* (2013.01); *A61B 5/742* (2013.01); *G06T 7/0012* (2013.01); *G06T 11/60* (2013.01)

(58) Field of Classification Search
 CPC ...................................................... G06T 11/00
 (Continued)

(56) References Cited

U.S. PATENT DOCUMENTS 6,322,516 B1 11/2001 Masuda et al.
6,884,221 B2 4/2005 Narimatsu et al.
(Continued)

FOREIGN PATENT DOCUMENTS

EP 1332715 A2 8/2003
EP 1374760 A2 1/2004
(Continued)

OTHER PUBLICATIONS

European Search Report for European Patent App. No. 14187764.7 (Dec. 19, 2014).
(Continued)

*Primary Examiner* — Gregory J Tryder
*Assistant Examiner* — Yi Yang
(74) *Attorney, Agent, or Firm* — Pearne & Gordon LLP

(57) ABSTRACT

A biological information displaying apparatus includes: a calculator which is configured to calculate measurement values of parameters based on a plurality of biological signals obtained by an acquiring unit, the parameters including: sclerosis parameters relating to arterial sclerosis; and stenosis and/or occlusion parameters relating to arterial stenosis and/or occlusion; a display which is configured to display information; and a display controller which is configured to produce different radar charts of the sclerosis parameters and the stenosis and/or occlusion parameters, and which is configured to display the measurement values of the parameters on the display, on respective one of line segments that radially extend from a center in each of the radar charts, while plotting each of the measurement values of corresponding parameters at a position that is remoter from the center as a clinical value is worse.

11 Claims, 9 Drawing Sheets

(51) Int. Cl.
  *G06T 11/20* (2006.01)
  *G06T 7/00* (2017.01)
  *A61B 5/00* (2006.01)
  *A61B 5/02* (2006.01)

(58) Field of Classification Search
  USPC .......................................................... 345/630
  See application file for complete search history.

(56) References Cited

U.S. PATENT DOCUMENTS

| | | | |
|---|---|---|---|
| 7,125,386 | B2 | 10/2006 | Kasahara |
| 9,044,145 | B2 | 6/2015 | Mori et al. |
| 2003/0236464 | A1* | 12/2003 | Narimatsu ............. A61B 5/021 |
| | | | 600/485 |
| 2004/0064071 | A1 | 4/2004 | Kasahara |
| 2005/0182333 | A1* | 8/2005 | Nagata ................. A61B 5/0432 |
| | | | 600/509 |
| 2006/0258943 | A1* | 11/2006 | Ogawa .................. A61B 5/022 |
| | | | 600/485 |
| 2007/0046671 | A1* | 3/2007 | Iguchi ................. G06F 3/04845 |
| | | | 345/440 |
| 2009/0161217 | A1* | 6/2009 | Mimura ................. G02B 5/124 |
| | | | 359/530 |
| 2011/0201902 | A1 | 8/2011 | Shiga et al. |
| 2012/0095353 | A1* | 4/2012 | Mori .................. A61B 5/02007 |
| | | | 600/500 |

FOREIGN PATENT DOCUMENTS

| | | |
|---|---|---|
| EP | 1488739 A1 | 12/2004 |
| JP | H06-215011 A | 8/1994 |
| JP | H11-318841 A | 11/1999 |
| JP | 2002-230174 A | 8/2002 |
| JP | 2004-016746 A | 1/2004 |
| JP | 2004-081621 A | 3/2004 |
| JP | 2006-320701 A | 11/2006 |
| JP | 2010-122901 A | 6/2010 |
| JP | 2011-092556 A | 5/2011 |

OTHER PUBLICATIONS

Japanese Office Action issued in Patent Application No. JP 2013-214509 dated Jan. 16, 2017.

* cited by examiner

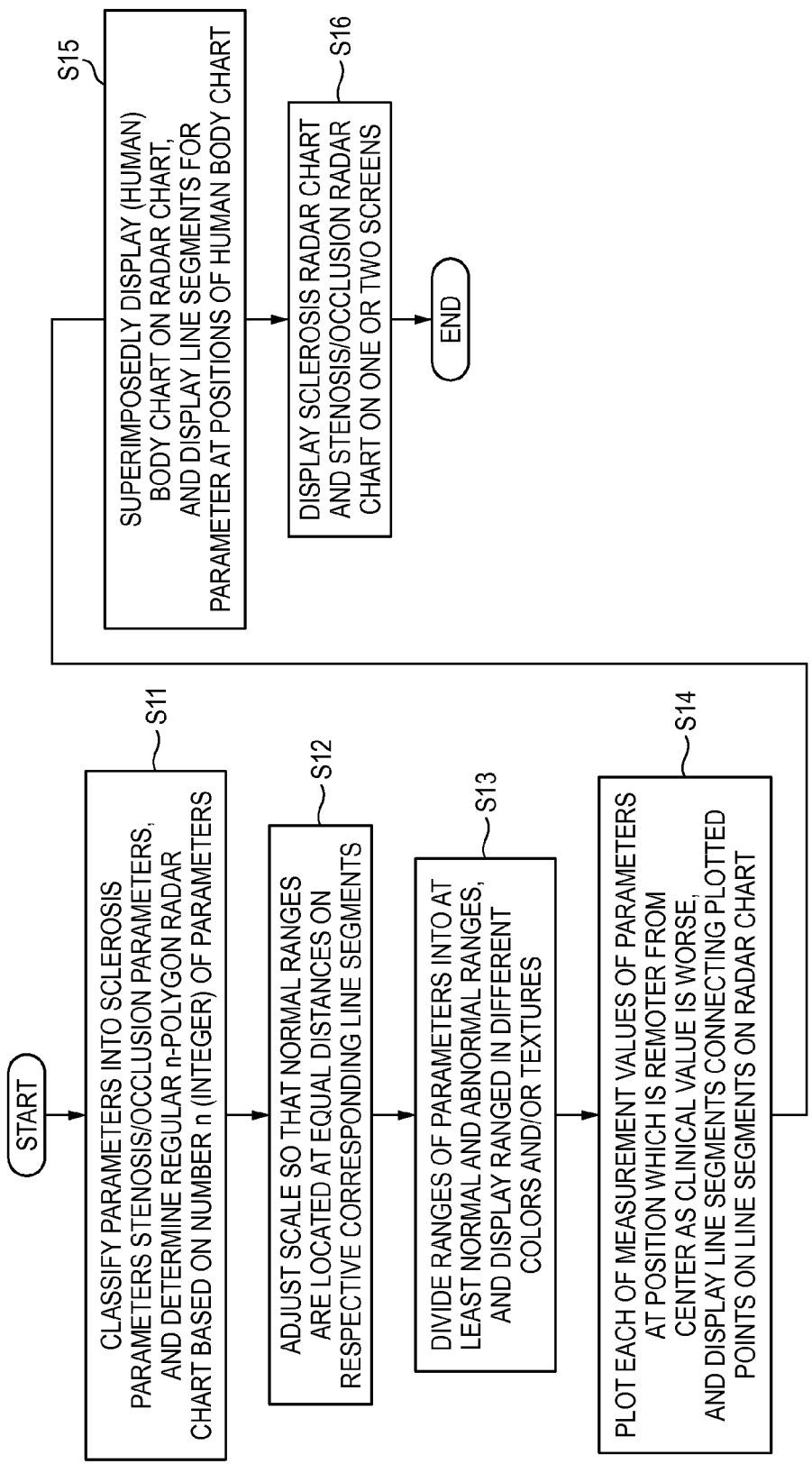

FIG. 3

| POSITION INFORMATION (HUMAN BODY CHART) |
|---|
| R: RIGHT<br>L: LEFT<br>RB: RIGHT BRACHIAL<br>LB: LEFT BRACHIAL<br>RA: RIGHT ANKLE<br>LA: LEFT ANKLE |

| PARAMETERS |
|---|
| SCLEROSIS PARAMETER<br><br>Stiffness$\beta$ MBP: MEAN ARTERIAL PRESSURE<br>PP: PULSE PRESSURE<br>API: Atrial Pressure volume Index<br>AVI: Atrial Velocity pulse Index |
| STENOSIS/OCCLUSION PARAMETER<br><br>%MAP: %Mean Arterial Pressure UT: upstroke time<br>ABI: Ankle Brachial Index<br>SBP \| R-L \|: SYSTOLIC BLOOD PRESSURE DIFFERENCE<br>               BETWEEN RIGHT AND LEFT UPPER ARMS<br>IAD-SBP: INTER ARM DIFFERENCE SYSTOLIC BLOOD<br>          PRESSURE |

FIG. 7
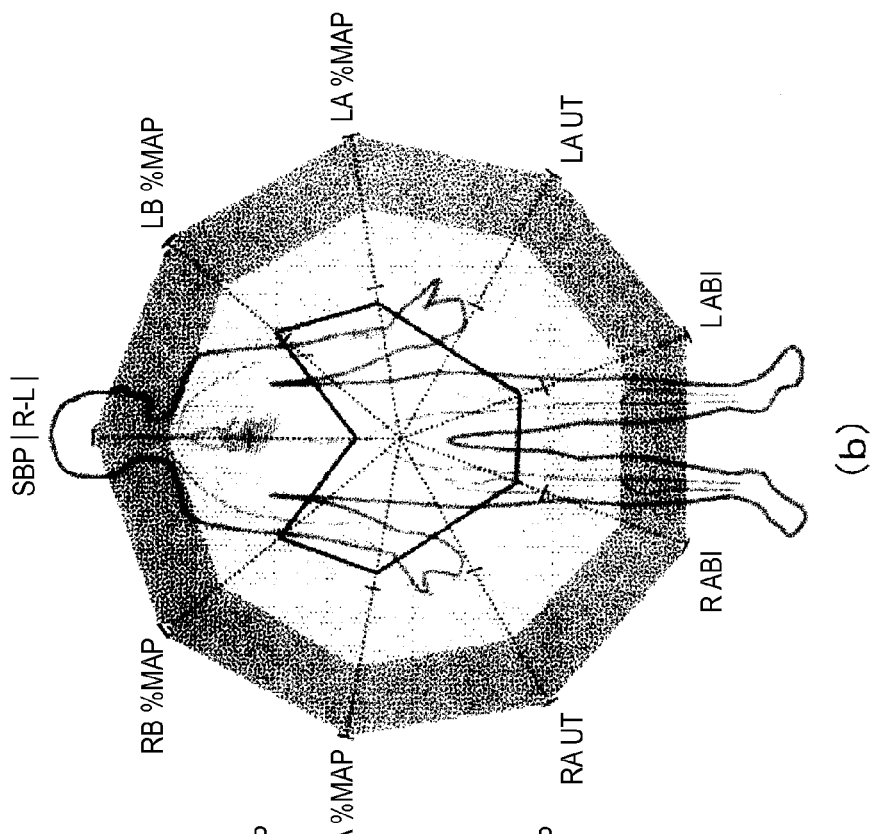
STENOSIS/OCCLUSION RADAR CHART
(b)
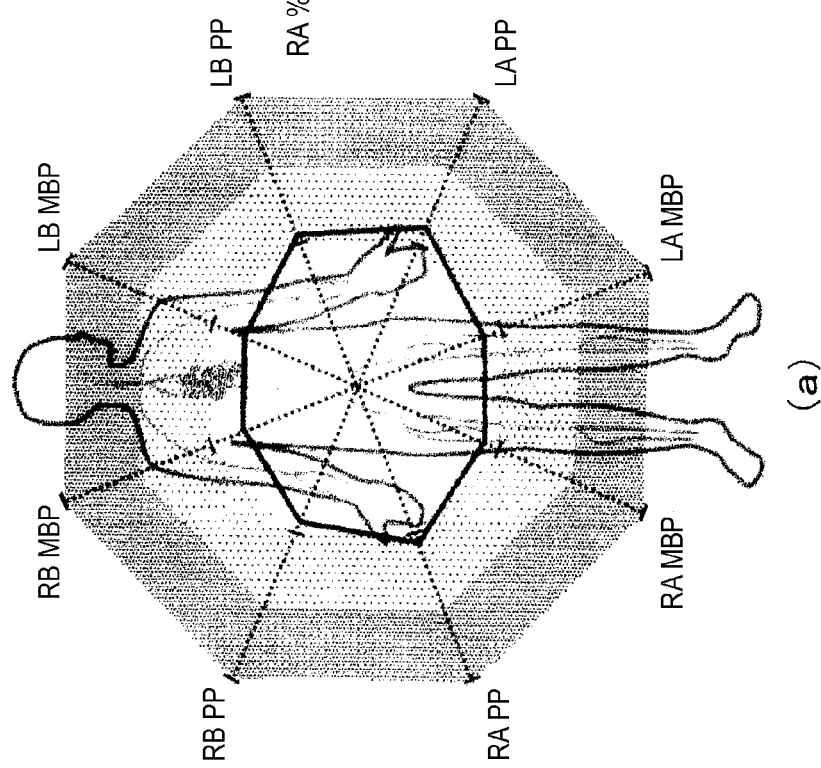
SCLEROSIS RADAR CHART
(a)

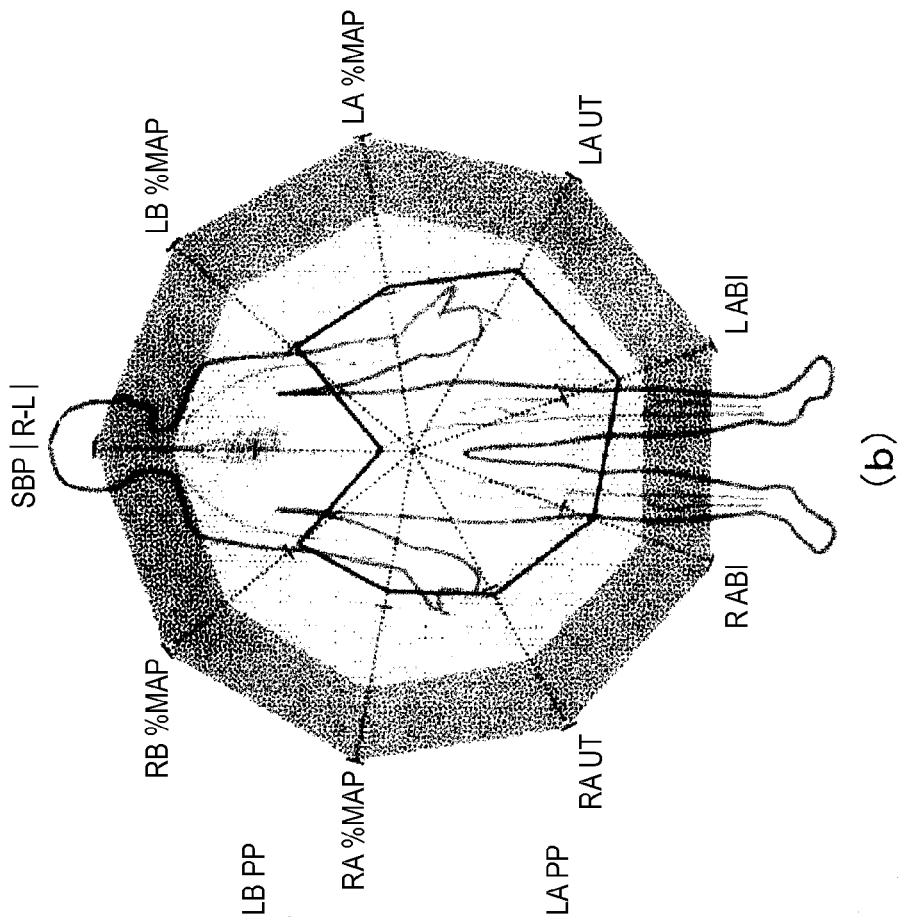
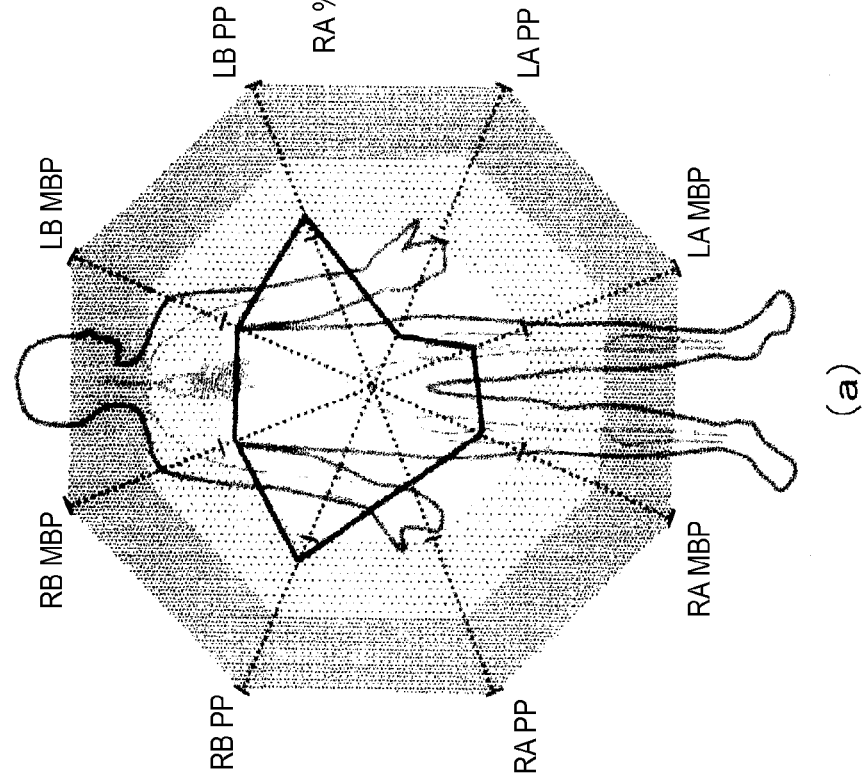
FIG. 9

BIOLOGICAL INFORMATION DISPLAYING APPARATUS AND BIOLOGICAL INFORMATION DISPLAYING METHOD

CROSS-REFERENCE TO RELATED APPLICATION(S)

This application is based upon and claims the benefit of priority from prior Japanese patent application No. 2013-214509, filed on Oct. 15, 2013, the entire contents of which are incorporated herein by reference.

BACKGROUND

The presently disclosed subject matter relates to a biological information displaying apparatus which adequately displays measurement values of a plurality of parameters relating to the condition of the artery and/or the cardiac function, and also to a biological information displaying method.

As parameters of measurement values indicating the condition of the artery, specifically the degrees of the distensibility and blood flow interruption of the artery, there are ABI, % MAP, UT, mean arterial pressure, pulse pressure, Stiffness Parameter $\beta$, API, AVI, AI, TBI, PWV, and the like. These parameters are used in diagnosis of vascular disease. As parameters of measurement values indicating the degree of the cardiac function, EF, SV, CO, % FS, mVef, TMF, Vp, Ea, Tei index, and the like are used.

With respect to measurement values of the parameters, only one parameter is displayed. Moreover, measurement values of the parameters are independently used in diagnosis. In such handling of measurement values, in the case where the distensibility or blood flow interruption of the artery, or abnormality of cardiac function is to be diagnosed, the measurement values are often biased depending on the diseased part of the living body or the degree of the disease, and therefore diagnosis cannot be adequately performed.

There is a biological information report in which blood pressures measured in the four limbs are plotted on line segments that extend from the origin in upper right, upper left, lower right, and lower left directions, respectively, and the body portions and the measurement values can be intuitively known (see JP-A-2006-320701).

In the above-mentioned biological information report, it is described that a measurement value such as PWV may be additionally displayed. Basically, only the blood pressure is measured, and the report is not configured so that many kinds of parameters are simultaneously compared with one another.

SUMMARY

The presently disclosed subject matter may provide a biological information displaying apparatus and method that enable measurement values of many kinds of parameters to be adequately displayed, a measurement in which only one parameter is used and therefore large bias occurs, to be complemented, and a diagnosis to be correctly performed.

The biological information displaying apparatus may comprise: a calculator which is configured to calculate measurement values of parameters based on a plurality of biological signals obtained by an acquiring unit, the parameters including: sclerosis parameters relating to arterial sclerosis; and stenosis and/or occlusion parameters relating to arterial stenosis and/or occlusion; a display which is configured to display information; and a display controller which is configured to produce different radar charts of the sclerosis parameters and the stenosis and/or occlusion parameters, and which is configured to display the measurement values of the parameters on the display, on respective one of line segments that radially extend from a center in each of the radar charts, while plotting each of the measurement values of corresponding parameters at a position that is remoter from the center as a clinical value is worse.

The display controller may display the different radar charts on a same screen or on different screens of the display.

The display controller may display the radar charts while adjusting a scale so that normal ranges of the parameters are located at equal distances on the respective line segments.

The display controller may divide a range of each of the parameters in each of the radar charts into at least the normal and abnormal ranges, the ranges displayed in different colors or textures.

The biological information displaying apparatus may further comprise: an inputting unit through which the parameters are instructed and input. The display controller may display only the parameters which are instructed and input through the inputting unit, on the radar charts.

The display controller may superimposedly display a body chart on the radar chart, and display the line segment for corresponding one of the parameters at a position of the displayed body chart which corresponds to a measurement portion of the parameter.

The display controller may display line segments connecting the plotted points on the lines segments in each of the radar charts.

The biological information displaying method may comprise: producing different radar charts of sclerosis parameters relating to arterial sclerosis, and stenosis and/or occlusion parameters relating to arterial stenosis and/or occlusion; and displaying measurement values of the parameters on a display, on respective one of line segments that radially extend from a center in each of the radar charts, while plotting each of the measurement values of corresponding parameters at a position that is remoter from the center as a clinical value is worse.

The measurement values of the parameters may be calculated based on a plurality of biological signals that are obtained by an acquiring unit.

The different radar charts may be displayed on a same screen or on different screens of the display.

The radar charts may be displayed while adjusting a scale so that normal ranges of the parameters are located at equal distances on the respective line segments.

A range of each of the parameters in each of the radar charts may be divided into at least the normal and abnormal ranges, the ranges displayed in different colors or textures.

Only the parameters that are instructed and input through an inputting unit, may be displayed on the radar charts.

A body chart may be superimposedly displayed on the radar chart, and the line segment for corresponding one of the parameters may be displayed at a position of the displayed body chart which corresponds to a measurement portion of the parameter.

Line segments connecting the plotted points may be displayed on the lines segments in each of the radar charts.

There may be also provided a program causing a computer to execute the biological information displaying method.

There may be also provided a non-transitory computer-readable recording medium storing a program causing a computer to execute the biological information displaying method.

BRIEF DESCRIPTION OF THE DRAWINGS

FIG. 2 is a flowchart showing the operation of the embodiment of the biological information displaying apparatus of the presently disclosed subject matter.

FIG. 3 is a view showing an example of position information and parameter classification databases stored in a memory of the embodiment of the biological information displaying apparatus of the presently disclosed subject matter.

FIG. 7 is a view showing a display example which is produced and displayed by the embodiment of the biological information displaying apparatus of the presently disclosed subject matter, which contains two kinds of radar charts on one screen, and which is obtained in measurements on a healthy person.

FIG. 9 is a view showing a display example which is produced and displayed by the embodiment of the biological information displaying apparatus of the presently disclosed subject matter, which contains two kinds of radar charts on one screen, and which is obtained in measurements on a subject with stenosis in peripheral artery.

DETAILED DESCRIPTION OF EXEMPLARY EMBODIMENTS

Figure 1:
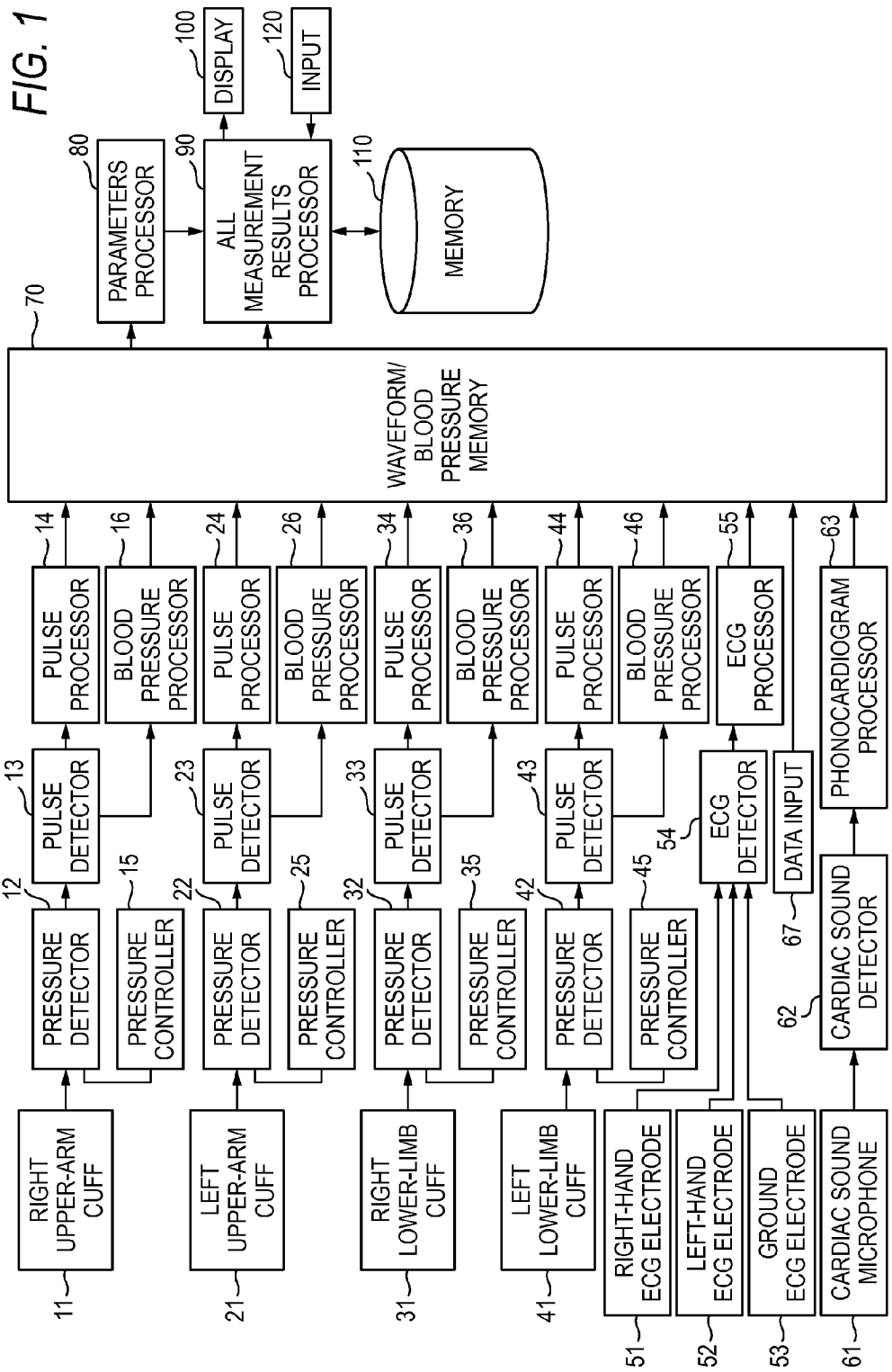
FIG. 1 is a configuration diagram of an embodiment of the biological information displaying apparatus of the presently disclosed subject matter.

Hereinafter, an embodiment of the biological information displaying apparatus and the biological information displaying method of the presently disclosed subject matter will be described with reference to the accompanying drawings. The identical components in the figures are denoted by the same reference numerals, and duplicated description is omitted. FIG. 1 is a configuration diagram of an embodiment of the biological information displaying apparatus of the presently disclosed subject matter. The apparatus includes sensors for obtaining measurement values of parameters relating to the condition of the artery and/or the cardiac function, i.e., sensors functioning as an acquiring unit for acquiring biological signals. As the sensors, a right brachial cuff 11, a left brachial cuff 21, a right lower-limb cuff 31, a left lower-limb cuff 41, a right-hand ECG electrode 51, a left-hand ECG electrode 52, a ground ECG electrode 53, and a cardiac sound microphone 61 are disposed. The sensors are mere examples, and the number of the sensors may be larger or smaller than that of the above sensors. Sensors which can acquire biological signals that are different from those in the embodiment may be disposed. In FIG. 1, a data input 67 is disposed as an acquiring unit for acquiring biological signals. Cardiac echo information is input through the data input 67. The cardiac echo information is stored in a waveform/blood pressure memory 70. Alternatively, a probe may be used as an acquiring unit for acquiring biological signals.

A pressure detector 12 is connected to the right brachial cuff 11, and the pressure of the right brachial cuff 11 is controlled by a pressure controller 15 through the pressure detector 12. A pressure detector 22 is connected to the left brachial cuff 21, and the pressure of the left brachial cuff 21 is controlled by a pressure controller 25 through the pressure detector 22. A pressure detector 32 is connected to the right lower-limb cuff 31, and the pressure of the right lower-limb cuff 31 is controlled by a pressure controller 35 through the pressure detector 32. A pressure detector 42 is connected to the left lower-limb cuff 41, and the pressure of the left lower-limb cuff 41 is controlled by a pressure controller 45 through the pressure detector 42. The pressure controllers 15, 25, 35, 45 may control the pressures of the respective cuffs under control of a computer which will be described later.

A pulse detector 13 is connected to the pressure detector 12, a pulse detector 23 is connected to the pressure detector 22, a pulse detector 33 is connected to the pressure detector 32, and a pulse detector 43 is connected to the pressure detector 42.

A pulse processor 14 for obtaining pulse data, and a blood pressure processor 16 for obtaining blood pressure data are connected to the pulse detector 13, a pulse processor 24 for obtaining pulse data, and a blood pressure processor 26 for obtaining blood pressure data are connected to the pulse detector 23, a pulse processor 34 for obtaining pulse data, and a blood pressure processor 36 for obtaining blood pressure data are connected to the pulse detector 33, and a pulse processor 44 for obtaining pulse data, and a blood pressure processor 46 for obtaining blood pressure data are connected to the pulse detector 43.

The right-hand ECG electrode 51, the left-hand ECG electrode 52, and the ground ECG electrode 53 are connected to an ECG detector 54, and an ECG processor 55 which obtains ECG data based on obtained ECG signals is connected to the ECG detector 54. A cardiac sound detector 62 is connected to the cardiac sound microphone 61, and a phonocardiogram processor 63 which obtains phonocardiogram data based on a cardiac sound signal is connected to the cardiac sound detector 62.

The pulse data obtained by the pulse processors 14, 24, 34, 44, the blood pressure data obtained by the blood pressure processors 16, 26, 36, 46, the ECG data obtained by the ECG processor 55, and the phonocardiogram data obtained by the phonocardiogram processor 63 are stored in the waveform/blood pressure memory 70. A parameters processor 80 is connected to the waveform/blood pressure memory 70. Calculations are performed on measurement values with respect to parameters relating to the condition of the artery and/or the cardiac function, by the parameters processor 80 functioning as a calculating unit. The parameters processor 80 can obtain by means of calculations all of the above-described parameters. Related-art techniques may be used as techniques for obtaining measurement values of the parameters. In the embodiment, description will be made while assuming that the parameters processor 80 obtains by means of calculations parameters indicated in radar charts and the like which will be described later.

Results of calculations performed by the parameters processor 80 are sent to an all measurement results processor 90. The all measurement results processor 90 can receive the results of calculations performed by the parameters processor 80, and in addition retrieve data from the waveform/blood pressure memory 70. The all measurement results processor 90 stores the results of calculations performed by the parameters processor 80, and data fetched from the waveform/blood pressure memory 70, in a memory 110 as required.

The memory 110 stores a parameter classification database in which parameters to be used in the apparatus are classified into sclerosis parameters relating to arterial sclerosis, and stenosis/occlusion parameters relating to arterial stenosis/occlusion. Also information of the normal and abnormal ranges, scale information for performing scale adjustment in which normal ranges of parameters are located at equal distances on respective corresponding line segments, and like information are stored in the memory 110.

Also a display 100 and an input 120 are connected to the all measurement results processor 90. The display 100 may be a display device which displays information on a screen, or a printer or the like. As the input 120, a keyboard (including that based on a touch panel) through which information or a command is input, or a pointing device such as a mouse may be disposed. The all measurement results processor 90 functions as a display controlling unit that, on the display 100, displays measurement values of parameters calculated by the parameters processor 80, as a radar chart in which, on respective one of the different line segments that radially extend from the center, each of the values is plotted at a position which is remoter from the center as the clinical value is worse. With respect to the ABI value, for example, a normal value is 1.0 to 1.4, an abnormal value is 0.9 or smaller, and a boundary value is 0.91 to 0.99. Therefore, the smaller the ABI value, the worse the clinical value. With respect to the % MAP value, for example, a normal value is smaller than 45%, and an abnormal value is 45% or larger. Therefore, the larger the % MAP value, the worse the clinical value.

The input 120 functions as an inputting unit through which parameters are instructed and input. The all measurement results processor 90 can operate as the display controlling unit so as to display only parameters which are instructed and input through the input 120 functioning as the inputting unit, in a radar chart.

The above-described components, i.e., the pulse processors 14, 24, 34, 44, the blood pressure processors 16, 26, 36, 46, the ECG processor 55, the phonocardiogram processor 63, the waveform/blood pressure memory 70, the parameters processor 80, the all measurement results processor 90, the display 100, the memory 110, and the input 120 may be configured as a computer.

The biological information displaying apparatus may operate in accordance with a program corresponding to the flowchart shown in FIG. 2. The program may be stored in a non-transitory computer-readable recording medium. In advance of measurements, the right brachial cuff 11, the brachial cuff 21, the right lower-limb cuff 31, the left lower-limb cuff 41, the right-hand ECG electrode 51, the left-hand ECG electrode 52, the ground ECG electrode 53, and the cardiac sound microphone 61 are attached to predetermined portions of the subject, such as the four limbs. When an ON/OFF switch or the like of the apparatus is operated, the apparatus starts to operate.

In the presently disclosed subject matter, parameters are displayed in a radar chart of sclerosis parameters relating to arterial sclerosis, and that of stenosis/occlusion parameters relating to arterial stenosis/occlusion. In the embodiment, based on data of the parameter classification database in the memory 110, a plurality of parameters are classified into sclerosis parameters relating to arterial sclerosis, and stenosis/occlusion parameters relating to arterial stenosis/occlusion, and then displayed in different radar charts. As a result, a sclerosis radar chart of the sclerosis parameters is displayed, and results of measurements relating to the distensibility of the artery can be collectively observed, so that the state of arterial sclerosis can be easily known. Moreover, a stenosis/occlusion radar chart of stenosis/occlusion parameters is displayed, and results of measurements relating to blood flow interruption due to stenosis or occlusion can be collectively observed, so that the state of blood flow interruption can be easily known.

The all measurement results processor 90 (display controlling unit) determines, with respect to each of sclerosis parameters and stenosis/occlusion parameters which have been classified, a radar chart having a regular n-polygonal shape based on the number n (integer) of parameters which are predetermined, or which are instructed and input through the input 120 at this timing (S11). On the line segments which radially extend from the center of the regular n-polygon to the vertices, respectively, next, measurement values of corresponding parameters are plotted, and scale adjustment is performed so that the normal ranges of the parameters are located at equal distances on the respective line segments (S12).

With respect to each of the parameters, next, the range is divided into at least the normal and abnormal ranges, and an image is produced so that the ranges are displayed in different colors and/or textures (S13). On respective one of the different line segments which radially extend from the center, moreover, each of the measurement values of the parameters is plotted at a position which is remoter from the center as the clinical value is worse, and an image showing line segments connecting the plotted points on the line segments on the radar chart is produced (S14). Then, a body chart (in the embodiment, a human body chart) is superimposedly displayed on the radar chart, and the line segment for corresponding one of the parameters is displayed at a position of the displayed human body chart which corresponds to the measurement portion of the parameter (S15).

In the embodiment, as described above, parameters are displayed on the different radar charts while being classified into sclerosis parameters relating to arterial sclerosis, and stenosis/occlusion parameters relating to arterial stenosis/occlusion. It is possible to switchingly select a display mode in which the different radar charts are displayed on one screen, or that in which the radar charts are displayed on two different screens, respectively. The selection can be performed through the input 120. In the case where the display on two different screens is selected, it is possible to select one of the stenosis/occlusion radar chart and the stenosis/occlusion radar chart to be displayed, through the input 120, and therefore the two radar charts can be switchingly displayed so as to be visually observed. Namely, the images which are produced in the steps preceding step S15 are displayed on one screen, or separately displayed on two different screens (S16).

The process sequence from step S12 to step S15 is not limited to the above-described sequence.

In the above-described process, for example, IAD-SBP, MBP (RB, LB, RA, LA), UT (RA, LA), AVI (RB, LB, RA, LA), PP (RB, LB, RA, LA), % MAP (RB, LB, RA, LA), and ABI (R, L) are set as parameters. The parameter classification database of the memory 110 stores data shown in FIG. 3. In FIG. 3, the contents indicated on the right side of each colon are not required to be stored. With respect to R, L, RB, LB, RA, and LA, the contents indicated on the right side of each of the colons are set as position information relating to a manner of displaying a line segment for a parameter correspondingly to a position of the human body chart.

In the thus set parameters, according to the parameter classification database of FIG. 3, it can be determined that MBP, PP, and AVI are sclerosis parameters, and IAD-SBP, % MAP, UT, and ABI are stenosis/occlusion parameters. Therefore, the parameters are classified into (MBP, PP, AVI) and (IAD-SBP, % MAP, UT, ABI). With respect to (MBP, PP, AVI), it is determined from the display position information that the whole parameter number is 12, and a regular dodecagon is to be displayed. With respect to (IAD-SBP, % MAP, UT, ABI), furthermore, it is determined from the display position information that the whole parameter number is 9, and a regular enneagon is to be displayed. The above operations are performed in step S11.

Figure 4:
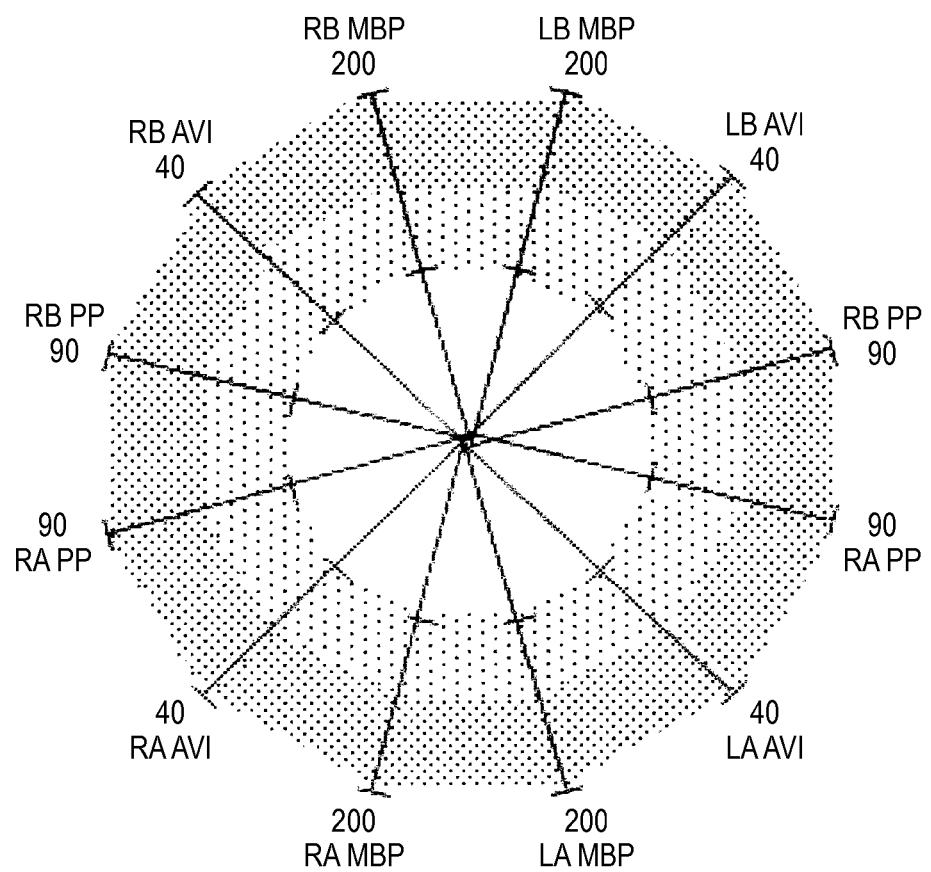
FIG. 4 is a view showing an example of a sclerosis radar chart before completion which is produced by the embodiment of the biological information displaying apparatus of the presently disclosed subject matter.
Figure 5:
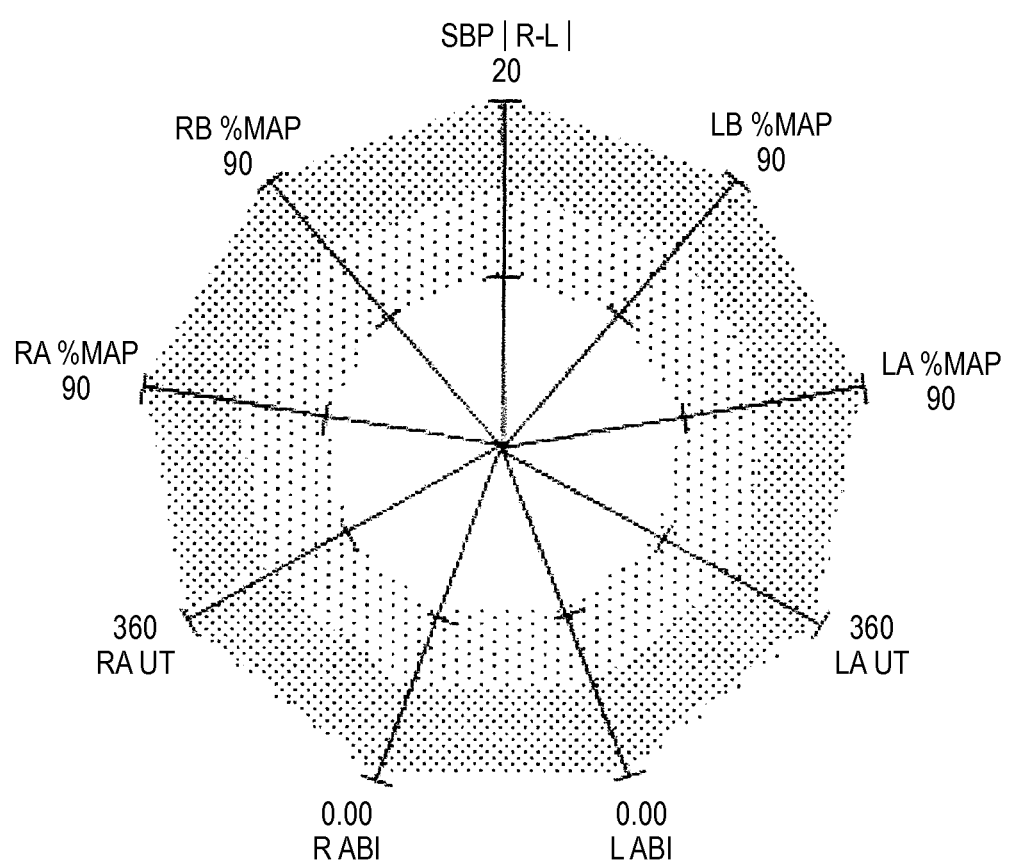
FIG. 5 is a view showing an example of a stenosis/occlusion radar chart before completion which is produced by the embodiment of the biological information displaying apparatus of the presently disclosed subject matter.

On the line segments which extend from the center of the polygon to the vertices, respectively, next, measurement values of corresponding parameters are plotted, and scale adjustment is performed so that the normal ranges of the parameters are located at equal distances on the respective corresponding line segments (S12). Then, the parameter ranges are divided into at least the normal and abnormal ranges, and an image is produced so that the ranges are displayed in different colors and/or textures (S13). The measurement value of each of the parameters is plotted, and an image showing line segments connecting the plotted points is produced (S14). As a result, an image of the sclerosis radar chart is produced as shown in FIG. 4, and that of the stenosis/occlusion radar chart is produced as shown in FIG. 5. As shown in FIGS. 4 and 5, position information and parameter identifications are additionally displayed in the vicinities of the vertices of the regular n-polygon.

Figure 6:
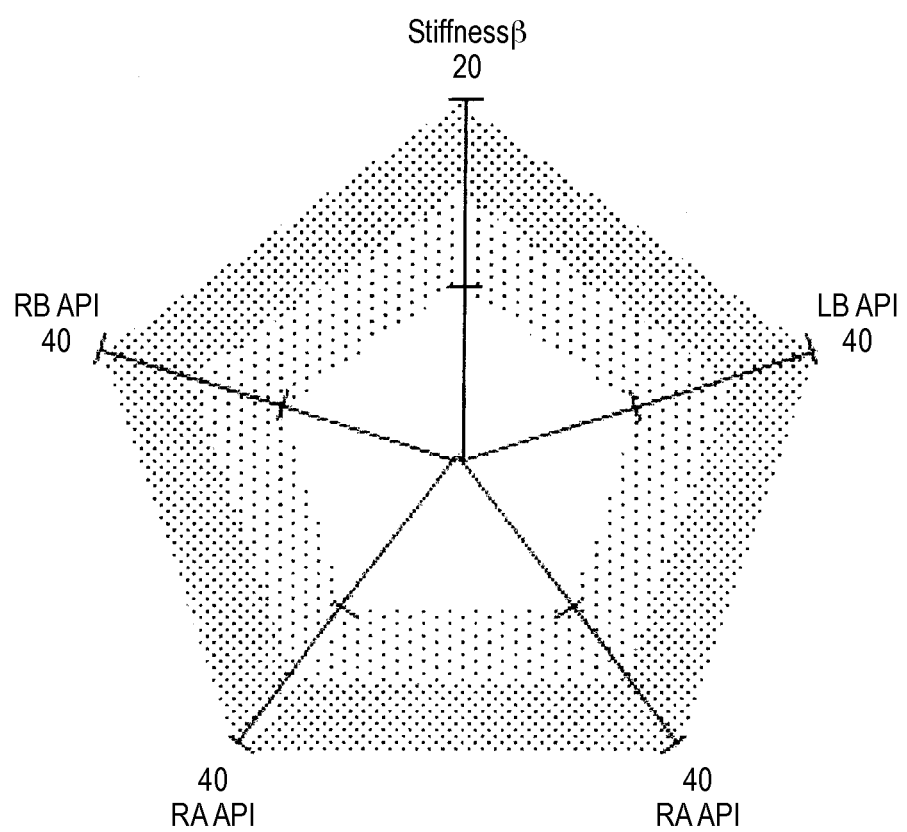
FIG. 6 is a view showing an example of a sclerosis radar chart before completion which is produced by the embodiment of the biological information displaying apparatus of the presently disclosed subject matter, the example being different from that of FIG. 4.

FIG. 6 is a view showing a sclerosis radar chart in the case where Stiffness β and API (RB, LB, RA, LA) which are sclerosis parameters are set as parameters. In this example, it is determined from the parameters and the position information that the whole parameter number is 5, and a regular pentagon is to be displayed. In order to measure Stiffness β which is a sclerosis parameter, the apparatus of the embodiment of FIG. 1 further includes an ultrasonic echo sensor, ultrasonic transmitter/receiver, ultrasonic controller/processor, and the like which measure the vessel diameter of the carotid artery.

Figure 8:
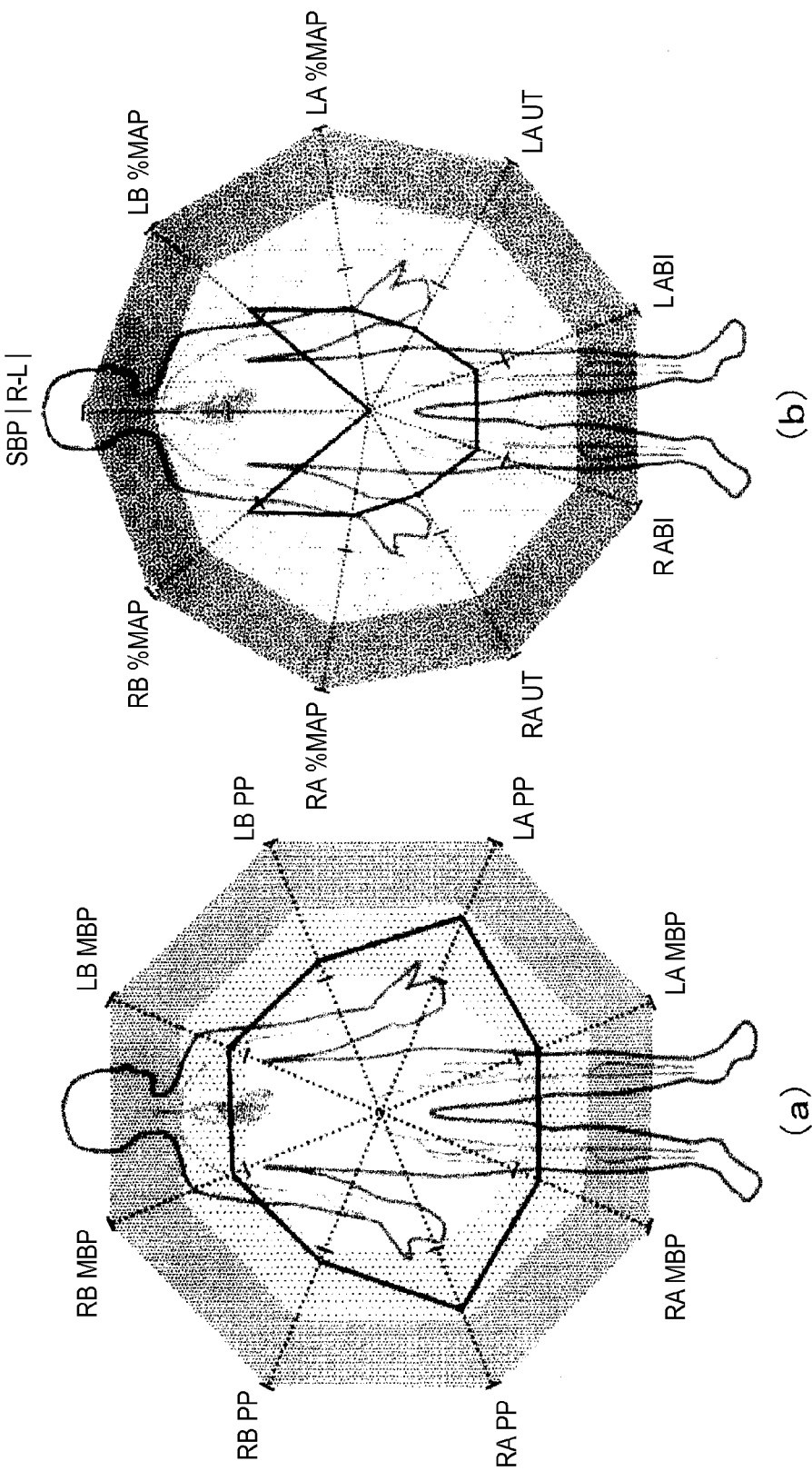
FIG. 8 is a view showing a display example which is produced and displayed by the embodiment of the biological information displaying apparatus of the presently disclosed subject matter, which contains two kinds of radar charts on one screen, and which is obtained in measurements on a subject showing the signs of arterial sclerosis.

FIGS. 4 to 6 show the images obtained in the processes of steps S11 to S13. By contrast, FIGS. 7 to 9 show examples in which the images obtained in the processes of steps S11 to S16 are displayed on one screen. In the examples of FIGS. 7A to 9B, MBP (RB, LB, RA, LA) and PP (RB, LB, RA, LA) are set as sclerosis parameters, and IAD-SBP, % MAP (RB, LB, RA, LA), UT (RA, LA), and ABI (R, L) are set asstenosis/occlusion parameters. In this example, with respect to the sclerosis parameters, it is determined from the parameters and the position information that the whole parameter number is 8, and a regular octagon is to be displayed. With respect to the stenosis/occlusion parameters, it is determined from the parameters and the position information that the whole parameter number is 9, and a regular enneagon is to be displayed.

FIG. 7 shows parameters of a healthy person. In the sclerosis radar chart shown in (a) of FIG. 7 and the stenosis/occlusion radar chart shown in (b) of FIG. 7, it is clearly seen at a glance that the line segments connecting the plotted points are within the normal range.

FIG. 8 shows parameters of a subject showing the signs of arterial sclerosis. In the sclerosis radar chart shown in (a) of FIG. 8, the line segments connecting the plotted points are remarkably deviated from the normal range, and it is clearly seen at a glance that the subject has a sclerosis problem. By contrast, in the stenosis/occlusion radar chart shown in (b) of FIG. 8, it is clearly seen at a glance that the line segments connecting the plotted points are within the normal range.

FIG. 9 shows parameters of a subject with stenosis in peripheral artery. In the sclerosis radar chart shown in (a) of FIG. 9, it is clearly seen at a glance that the line segments connecting the plotted points are within the normal range. By contrast, in the stenosis/occlusion radar chart shown in (b) of FIG. 9, the line segments connecting the plotted points are remarkably deviated from the normal range, and it is clearly seen at a glance that the subject has a stenosis/occlusion problem.

In the embodiment, as described above, it is clearly seen at a glance whether, in the sclerosis radar chart and the stenosis/occlusion radar chart, measurement values are within the normal range or not. Therefore, it can be expected that the apparatus will be useful in adequate diagnosis.

In the embodiment, the biological information displaying apparatus has the sensors, and biological information obtained by the sensors are processed in real time. However, the presently disclosed subject matter is not limited to this. For example, biological information which is previously measured may be processed. Alternatively, biological information obtained by another apparatus or the like may be input or transferred to the biological information displaying apparatus, and the biological information may be processed.

In the examples of FIGS. 7 to 9, a human body chart is displayed superimposedly on a radar chart. However, the invention is not limited to this. In place of a human body chart, another body chart such as a heart chart may be superimposedly displayed.

In the examples of FIGS. 7 to 9, a sclerosis radar chart and a stenosis/occlusion radar chart are displayed in a juxtaposed manner. Furthermore, an image in which a heart chart is superimposed on a radar chart relating to the cardiac function may be added.

According to an aspect of the presently disclosed subject matter, measurement values of parameters are displayed on the display in the form of a radar chart in which, on respective one of the different line segments that radially extend from the center, each of the values is plotted at a position which is remoter from the center as the clinical value is worse. Consequently, a measurement in which one parameter is used and therefore large bias occurs can be complemented, and a diagnosis can be correctly performed. According to an aspect of the presently disclosed subject matter, furthermore, a body chart is superimposedly displayed on the radar chart, and the line segment for corresponding one of the parameters is displayed at a position of the displayed body chart which corresponds to the measurement portion of the parameter. Therefore, measurement values of a plurality of parameters are displayed so as to correspond to the measurement portions, respectively. The condition of the artery and/or the cardiac function can be diagnosed while intuitively knowing relationships with the positions in the living body.

What is claimed is:

1. A biological information displaying apparatus comprising:
    a display which is configured to display information; and a processor configured to:
calculate measurement values of parameters based on a plurality of biological signals obtained by the processor, the parameters being classified into sclerosis parameters relating to arterial sclerosis, and stenosis and/or occlusion parameters relating to arterial stenosis and/or occlusion;
produce different radar charts of the sclerosis parameters and the stenosis and/or occlusion parameters; and
display the measurement values of the parameters on the display, on respective one of line segments that radially extend from a center in each of the radar charts, while plotting each of the measurement values of corresponding parameters at a position that is remoter from the center as a clinical value is worse;
display the radar charts while adjusting a scale so that normal ranges of the parameters are located at equal distances on the respective line segments;
divide a range of each of the parameters in each of the radar charts into at least the normal ranges and abnormal ranges, so that the normal ranges and the abnormal ranges are displayed in different colors and/or textures;
superimposedly display a body chart on the radar chart; and
display the line segment for a corresponding one of the parameters at a position of the displayed body chart which corresponds to a measurement portion of the parameter,
wherein the different radar charts include a sclerosis radar chart on which the sclerosis parameters are collectively displayed and a stenosis/occlusion radar chart on which the stenosis and/or occlusion parameters are collectively displayed.

2. The biological information displaying apparatus according to claim 1, wherein the processor is further configured to display the different radar charts on a same screen or on different screens of the display.

3. The biological information displaying apparatus according to claim 1, further comprising: an inputting unit through which the parameters are instructed and input, wherein the processor is further configured to display only the parameters which are instructed and input through the inputting unit, on the radar charts.

4. The biological information displaying apparatus according to claim 1, wherein the processor is further configured to display line segments connecting the plotted points on the lines segments in each of the radar charts.

5. A biological information displaying method comprising:
producing different radar charts of parameters, the parameters being classified into sclerosis parameters relating to arterial sclerosis, and stenosis and/or occlusion parameters relating to arterial stenosis and/or occlusion; and
displaying measurement values of the parameters on a display, on respective one of line segments that radially extend from a center in each of the radar charts, while plotting each of the measurement values of corresponding parameters at a position that is remoter from the center as a clinical value is worse,
wherein the different radar charts include a sclerosis radar chart on which the sclerosis parameters are collectively displayed and a stenosis/occlusion radar chart on which the stenosis and/or occlusion parameters are collectively displayed,
wherein the radar charts are displayed while adjusting a scale so that normal ranges of the parameters are located at equal distances on the respective line segments,
wherein a range of each of the parameters in each of the radar charts is divided into at least the normal ranges and abnormal ranges, so that the normal ranges and the abnormal ranges are displayed in different colors and/or textures,
wherein a body chart is superimposedly displayed on the radar chart, and
wherein the line segment for a corresponding one of the parameters is displayed at a position of the displayed body chart which corresponds to a measurement portion of the parameter.

6. The biological information displaying method according to claim 5, wherein the measurement values of the parameters are calculated based on a plurality of biological signals that are obtained by an acquiring unit.

7. The biological information displaying method according to claim 5, wherein the different radar charts are displayed on a same screen or on different screens of the display.

8. The biological information displaying method according to claim 5, wherein only the parameters that are instructed and input through an inputting unit, are displayed on the radar charts.

9. The biological information displaying method according to claim 5, wherein line segments connecting the plotted points are displayed on the lines segments in each of the radar charts.

10. A non-transitory computer-readable medium that stores instructions that, when executed, cause a computer to execute the biological information displaying method according to claim 5.

11. A non-transitory computer-readable recording medium storing a program causing a computer to execute the biological information displaying method according to claim 5.

* * * * *